(12) United States Patent
Cabot

(10) Patent No.: US 12,114,689 B2
(45) Date of Patent: Oct. 15, 2024

(54) GEL AND CRYSTALLINE POWDER

(71) Applicant: NICOVENTURES TRADING LIMITED, London (GB)

(72) Inventor: Ross Cabot, London (GB)

(73) Assignee: NICOVENTURES TRADING LIMITED, London (GB)

( * ) Notice: Subject to any disclaimer, the term of this patent is extended or adjusted under 35 U.S.C. 154(b) by 677 days.

(21) Appl. No.: 17/290,372

(22) PCT Filed: Oct. 31, 2019

(86) PCT No.: PCT/GB2019/053090
§ 371 (c)(1),
(2) Date: Apr. 30, 2021

(87) PCT Pub. No.: WO2020/089636
PCT Pub. Date: May 7, 2020

(65) Prior Publication Data
US 2022/0273019 A1    Sep. 1, 2022

(30) Foreign Application Priority Data

Nov. 1, 2018  (GB) ...................................... 1817861

(51) Int. Cl.
*A24B 15/167*  (2020.01)
*A24B 15/28*  (2006.01)
(Continued)

(52) U.S. Cl.
CPC .......... *A24B 15/167* (2016.11); *A24B 15/283* (2013.01); *A24B 15/32* (2013.01); *A24F 40/10* (2020.01)

(58) Field of Classification Search
None
See application file for complete search history.

(56) References Cited

U.S. PATENT DOCUMENTS

| 4,195,645 A | 4/1980 | Bayless et al. |
| 4,574,151 A | 3/1986 | Adams |

(Continued)

FOREIGN PATENT DOCUMENTS

| CN | 101390659 | 3/2009 |
| JP | S46-027357 | 8/1971 |

(Continued)

OTHER PUBLICATIONS

International Search Report and Written Opinion for PCT/GB2019/053090 date mailed Feb. 18, 2020.

(Continued)

*Primary Examiner* — Philip Y Louie
*Assistant Examiner* — Madeleine P Delacruz
(74) *Attorney, Agent, or Firm* — WOMBLE BOND DICKINSON (US) LLP

(57) ABSTRACT

A gel comprising (i) water in an amount of from 1 to 20 wt. % based on the gel; (ii) nicotine; and (iii) a water soluble acid. The is further provided a crystalline powder comprising (i) water in an amount of less than 15% wt. % based on the crystalline powder; (ii) nicotine; (iii) a water soluble acid; (iv) one or more flavors; and (v) an encapsulating material. Processes for forming the gel and the crystalline powder include dehydrating a nicotine solution to provide the gel and crystalline powder, and processes for rehydrating the gel and the crystalline powder include contacting the gel and the crystalline powder with water.

19 Claims, 1 Drawing Sheet

(51) Int. Cl.
     A24B 15/32    (2006.01)
     A24B 15/34    (2006.01)
     A24B 15/40    (2006.01)
     A24F 40/10    (2020.01)
     A61K 31/465   (2006.01)

(56)           References Cited

U.S. PATENT DOCUMENTS 5,046,514    A      9/1991   Bolt
     5,362,496    A     11/1994   Baker et al.
     5,778,899    A      7/1998   Saito et al.
     6,110,495    A      8/2000   Dam
     6,258,341    B1     7/2001   Foster et al.
     9,375,033    B2     6/2016   Lampe et al.
     9,775,376    B2    10/2017   Cantrell et al.
    10,556,880    B2     2/2020   Dull et al.
    2008/0287507  A1    11/2008   Hedenstrom et al.
    2012/0325228  A1*   12/2012   Williams ............. A24B 15/167
                                                              131/328
    2013/0004542  A1     1/2013   Martyn
    2013/0074855  A1     3/2013   Holton
    2014/0060554  A1*    3/2014   Collett .................. A24F 40/30
                                                              392/386
    2015/0230515  A1*    8/2015   Lampe ................. A23G 4/068
                                                              131/352
    2015/0306623  A1    10/2015   Kawano et al.

2016/0120225  A1*    5/2016   Mishra ................... A24F 40/42
                                                              392/386
    2016/0198759  A1     7/2016   Kuntawala et al.
    2016/0338407  A1    11/2016   Kerdemelidis
    2017/0303594  A1    10/2017   Cameron et al.
    2017/0325494  A1    11/2017   Cameron et al.
    2017/0334881  A1    11/2017   Dull et al.
    2018/0289907  A1    10/2018   Marmur et al.

FOREIGN PATENT DOCUMENTS

JP         H07-155161         6/1995
    KR         20160008271        1/2016
    WO         2007037962         4/2007
    WO         WO2014182736      11/2014
    WO         WO2015006652       1/2015
    WO         WO2016071705       5/2016
    WO         WO2016071706       5/2016

OTHER PUBLICATIONS

Clayton P M et al., Spectroscopic investigations into the acid-base properties of nicotine at different temperatures, Anal Methods, 2013, vol. 5, pp. 81-88.
Riggs D M et al., "Thermochemical Properties of Nicotine Salts", Beiträge zur Tabakforschung International/Contributions to Tobacco Research, Jul. 1, 2001, vol. 19, No. 6, pp. 289-295.

* cited by examiner

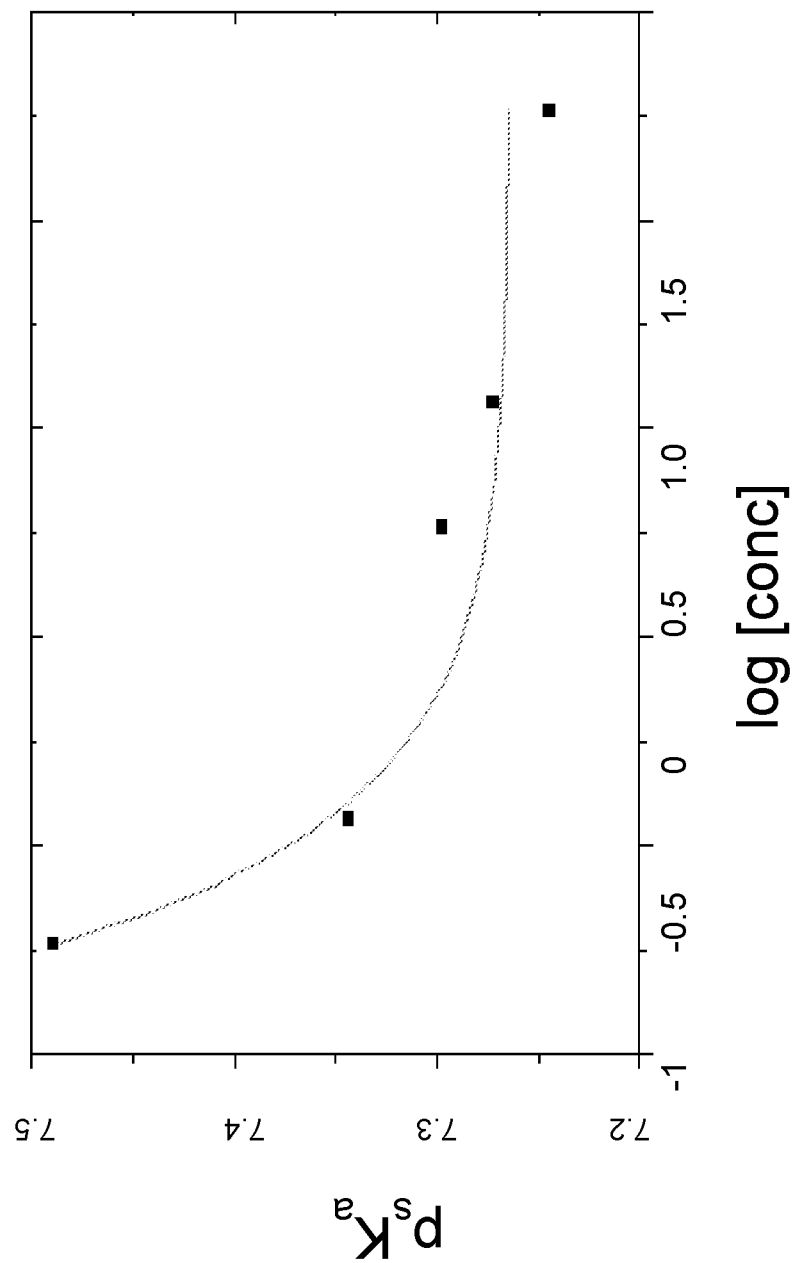

GEL AND CRYSTALLINE POWDER

PRIORITY CLAIM

The present application is a National Phase entry of PCT Application No. PCT/GB2019/053090, filed Oct. 31, 2019 which claims priority from GB Patent Application No. 1817861.6 filed Nov. 1, 2018, each of which is hereby fully incorporated herein by reference.

FIELD OF THE INVENTION

The present disclosure relates to a gel and to a crystalline powder, a method of forming the same, a container containing the same, a device containing the same and processes and uses of the same.

BACKGROUND TO THE INVENTION

Electronic aerosol provision systems such as e-cigarettes generally contain a reservoir of liquid which is to be vaporized, typically containing nicotine. When a user inhales on the device, a heater is activated to vaporize a small amount of liquid, which is therefore inhaled by the user.

The use of e-cigarettes in the UK has grown rapidly, and it has been estimated that there are now over a million people using them in the UK.

One challenge faced in providing such systems is to provide from the aerosol provision device an aerosol to be inhaled which provides consumers with an acceptable experience. Some consumers may prefer an e-cigarette that generates an aerosol that closely 'mimics' smoke inhaled from a tobacco product such as a cigarette. Aerosols from e-cigarettes and smoke from tobacco products such as cigarettes provides to the user a complex chain of flavor in the mouth, nicotine absorption in the mouth and throat, followed by nicotine absorption in the lungs. These various aspects are described by users in terms of flavor, intensity/quality, impact, irritation/smoothness and nicotine reward. Nicotine contributes to a number of these factors, and is strongly associated with factors such as impact, irritation and smoothness; these are readily perceived by consumers, and e-cigarettes may offer too much or too little of these parameters for consumers, depending upon individual preferences. Nicotine reward is particularly complex as it results from both the amount of and speed with which nicotine is absorbed from the lining of the mouth, this is typically nicotine in the vapor phase, and from the amount and speed nicotine that is absorbed from the lungs, this is typically nicotine in the particulate phase of the aerosol which is inhaled. Each of these factors, and their balance, can strongly contribute to consumer acceptability of an e-cigarette. Providing means to optimize the overall vaping experience is therefore desirable to e-cigarette manufacturers.

SUMMARY OF THE INVENTION

In one aspect there is provided a gel comprising
(i) water in an amount of from 1 to 20 wt. % based on the gel;
(ii) nicotine; and
(iii) a water soluble acid.

In one aspect there is provided a crystalline powder comprising
(i) water in an amount of less than 15% wt. % based on the crystalline powder;
(ii) nicotine;
(iii) a water soluble acid;
(iv) one or more flavors; and
(v) an encapsulating material.

In one aspect there is provided a process for forming a gel comprising
(i) water in an amount of from 1 to 20 wt. % based on the gel;
(ii) nicotine; and
(iii) a water soluble acid;
the process comprising the steps of:
(a) providing a nicotine solution comprising
(i) water in an amount of from 50 to 90 wt. % based on the nicotine solution;
(ii) nicotine; and
(iii) the water soluble acid;
(b) dehydrating the nicotine solution to provide the gel.

In one aspect there is provided a process for forming a crystalline powder comprising
(i) water in an amount of less than 15 wt % based on the crystalline powder;
(ii) nicotine;
(iii) a water soluble acid;
(iv) one or more flavors; and
(v) an encapsulating material;
the process comprising the steps of:
(a) providing a nicotine solution comprising
(i) water in an amount of from 50 to 95 wt. % based on the nicotine solution;
(ii) nicotine;
(iii) a water soluble acid;
(iv) one or more flavors; and
(v) an encapsulating material;
(b) dehydrating the nicotine solution to provide the crystalline powder.

In one aspect there is provided a process for rehydrating a gel comprising
(i) water in an amount of from 1 to 20 wt. % based on the gel;
(ii) nicotine; and
(iii) a water soluble acid;
the process comprising the step of contacting the gel with water.

In one aspect there is provided a process for rehydrating a crystalline powder comprising
(i) water in an amount of less than 15% wt. % based on the crystalline powder;
(ii) nicotine;
(iii) a water soluble acid;
(iv) one or more flavors; and
(v) an encapsulating material;
the process comprising the step of contacting the crystalline powder with water.

In one aspect there is provided a contained gel comprising
(a) a container; and
(b) a gel, comprising
(i) water in an amount of from 1 to 20 wt. % based on the gel;
(ii) nicotine; and
(iii) a water soluble acid.

In one aspect there is provided a contained crystalline powder comprising
(a) a container; and
(b) a crystalline powder, comprising
(i) water in an amount of less than 15% wt. % based on the crystalline powder;
(ii) nicotine;

(iii) a water soluble acid;
(iv) one or more flavors; and
(v) an encapsulating material.

BRIEF DESCRIPTION OF THE DRAWINGS

The present disclosure will now be described in further detail by way of example only with reference to the accompanying FIGURE in which:

FIG. 1 shows a graph illustrating variation of $p_sK_{a2}$ with nicotine concentration.

DETAILED DESCRIPTION

As discussed herein in one aspect there is provided In one aspect there is provided a gel comprising (i) water in an amount of from 1 to 20 wt. % based on the gel; (ii) nicotine; and (iii) a water soluble acid. In a further aspect there is provided a crystalline powder comprising (i) water in an amount of less than 15% wt. % based on the crystalline powder; (ii) nicotine; (iii) a water soluble acid; (iv) one or more flavors; and (v) an encapsulating material.

We have found that an advantageous system may be provided which a gel is formed from nicotine; and a water soluble acid and this gel may be used in the formation of a crystalline powder comprising water, nicotine; water soluble acid; one or more flavors; and an encapsulating material. The gel is formed from a solution of nicotine, water a water soluble acid which is subsequently dehydrated to form the gel. The gel is readily transported without the need to transport unnecessary amounts of water. Gels are also easily handled and avoid the problems of leakage seen with liquids. When required, the gel may then be used to form a solution of water, nicotine; water soluble acid; one or more flavors; and an encapsulating material. This is achieved by contacting the gel with water, one or more flavors; and an encapsulating material. This process is further advantageous because the gel may be readily dissolved without heating. This avoids the loss of volatile nicotine and/or flavor. This further solution may be dehydrated to form a crystalline powder. This crystalline powder contains the necessary components to form an aerolizable liquid. The formation of this liquid may be performed by a manufacturer or by an end user. The crystalline powder is particularly advantageous because we have found that it will only dissolve when a sufficient amount of water is provided and thus any solution delivered will not be too concentrated in respect of nicotine. This is important to ensure that the end user is not provided with a nicotine solution which is undesirably concentrated.

For ease of reference, these and further aspects of the present disclosure are now discussed under appropriate section headings. However, the teachings under each section are not necessarily limited to each particular section.

As is understood by one skilled in the art, nicotine may exist in unprotonated form, monoprotonated form or diprotonated form. The structures of each of these forms are given below.

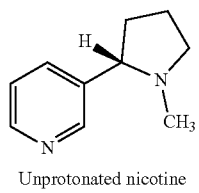
Unprotonated nicotine

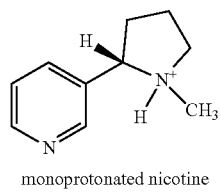
monoprotonated nicotine

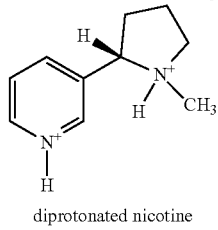
diprotonated nicotine

Reference in the specification to protonated form means both monoprotonated nicotine and diprotonated nicotine. Reference in the specification to amounts in the protonated form means the combined amount of monoprotonated nicotine and diprotonated nicotine. Furthermore, when reference is made to a fully protonated formulation it will be understood that at any one time there may be very minor amounts of unprotonated nicotine present, e.g. less than 1% unprotonated.

Water

As discussed herein the gel comprises water in an amount of from 1 to 20 wt. % based on the gel. In one aspect water is present in an amount of from 1 to 20 wt. % based on the gel. In one aspect water is present in an amount of from 1 to 15 wt. % based on the gel. In one aspect water is present in an amount of from 1 to 10 wt. % based on the gel.

As discussed herein the crystalline powder comprises water in an amount of less than 15 wt. % based on the crystalline powder. In one aspect water is present in an amount of less than 10 wt. % based on the crystalline powder. In one aspect water is present in an amount of less than 8 wt. % based on the crystalline powder.

Nicotine

Nicotine formulations may be provided having desirable properties of flavor, impact, irritation, smoothness and/or nicotine reward for the user.

In one aspect nicotine is present in an amount of no greater than 6 wt % based on the total weight of the crystalline powder. In one aspect nicotine is present in an amount of from 0.01 to 10 wt % based on the total weight of the crystalline powder. In one aspect nicotine is present in an amount of from 0.02 to 10 wt % based on the total weight of the crystalline powder. In one aspect nicotine is present in an amount of from 0.05 to 10 wt % based on the total weight of the crystalline powder. In one aspect nicotine is present in an amount of from 0.08 to 10 wt % based on the total weight of the crystalline powder. In one aspect nicotine is present in an amount of from 0.1 to 10 wt % based on the total weight of the crystalline powder. In one aspect nicotine is present in an amount of from 0.2 to 10 wt % based on the total weight of the crystalline powder. In one aspect nicotine is present in an amount of from 0.5 to 10 wt % based on the total weight of the crystalline powder. In one aspect nicotine is present in an amount of from 1 to 10 wt % based on the total weight of the crystalline powder.

In one aspect nicotine is present in an amount of no greater than 8 wt % based on the total weight of the crystalline powder. In one aspect nicotine is present in an amount of from 0.01 to 8 wt % based on the total weight of the crystalline powder. In one aspect nicotine is present in an amount of from 0.02 to 8 wt % based on the total weight of the crystalline powder. In one aspect nicotine is present in an amount of from 0.05 to 8 wt % based on the total weight of the crystalline powder. In one aspect nicotine is present in an amount of from 0.08 to 8 wt % based on the total weight of the crystalline powder. In one aspect nicotine is present in an amount of from 0.1 to 8 wt % based on the total weight of the crystalline powder. In one aspect nicotine is present in an amount of from 0.2 to 8 wt % based on the total weight of the crystalline powder. In one aspect nicotine is present in an amount of from 0.5 to 8 wt % based on the total weight of the crystalline powder. In one aspect nicotine is present in an amount of from 1 to 8 wt % based on the total weight of the crystalline powder.

In one aspect nicotine is present in an amount of no greater than 6 wt % based on the total weight of the crystalline powder. In one aspect nicotine is present in an amount of from 0.01 to 6 wt % based on the total weight of the crystalline powder. In one aspect nicotine is present in an amount of from 0.02 to 6 wt % based on the total weight of the crystalline powder. In one aspect nicotine is present in an amount of from 0.05 to 6 wt % based on the total weight of the crystalline powder. In one aspect nicotine is present in an amount of from 0.08 to 6 wt % based on the total weight of the crystalline powder. In one aspect nicotine is present in an amount of from 0.1 to 6 wt % based on the total weight of the crystalline powder. In one aspect nicotine is present in an amount of from 0.2 to 6 wt % based on the total weight of the crystalline powder. In one aspect nicotine is present in an amount of from 0.5 to 6 wt % based on the total weight of the crystalline powder. In one aspect nicotine is present in an amount of from 1 to 6 wt % based on the total weight of the crystalline powder.

In one aspect nicotine is present in an amount of no greater than 5 wt % based on the total weight of the crystalline powder. In one aspect nicotine is present in an amount of from 0.01 to 5 wt % based on the total weight of the crystalline powder. In one aspect nicotine is present in an amount of from 0.02 to 5 wt % based on the total weight of the crystalline powder. In one aspect nicotine is present in an amount of from 0.05 to 5 wt % based on the total weight of the crystalline powder. In one aspect nicotine is present in an amount of from 0.08 to 5 wt % based on the total weight of the crystalline powder. In one aspect nicotine is present in an amount of from 0.1 to 5 wt % based on the total weight of the crystalline powder. In one aspect nicotine is present in an amount of from 0.2 to 5 wt % based on the total weight of the crystalline powder. In one aspect nicotine is present in an amount of from 0.5 to 5 wt % based on the total weight of the crystalline powder. In one aspect nicotine is present in an amount of from 1 to 5 wt % based on the total weight of the crystalline powder.

In one aspect nicotine is present in an amount of no greater than 4 wt % based on the total weight of the crystalline powder. In one aspect nicotine is present in an amount of from 0.01 to 4 wt % based on the total weight of the crystalline powder. In one aspect nicotine is present in an amount of from 0.02 to 4 wt % based on the total weight of the crystalline powder. In one aspect nicotine is present in an amount of from 0.05 to 4 wt % based on the total weight of the crystalline powder. In one aspect nicotine is present in an amount of from 0.08 to 4 wt % based on the total weight of the crystalline powder. In one aspect nicotine is present in an amount of from 0.1 to 4 wt % based on the total weight of the crystalline powder. In one aspect nicotine is present in an amount of from 0.2 to 4 wt % based on the total weight of the crystalline powder. In one aspect nicotine is present in an amount of from 0.5 to 4 wt % based on the total weight of the crystalline powder. In one aspect nicotine is present in an amount of from 1 to 4 wt % based on the total weight of the crystalline powder.

In one aspect nicotine is present in an amount of no greater than 3 wt % based on the total weight of the crystalline powder. In one aspect nicotine is present in an amount of from 0.01 to 3 wt % based on the total weight of the crystalline powder. In one aspect nicotine is present in an amount of from 0.02 to 3 wt % based on the total weight of the crystalline powder. In one aspect nicotine is present in an amount of from 0.05 to 3 wt % based on the total weight of the crystalline powder. In one aspect nicotine is present in an amount of from 0.08 to 3 wt % based on the total weight of the crystalline powder. In one aspect nicotine is present in an amount of from 0.1 to 3 wt % based on the total weight of the crystalline powder. In one aspect nicotine is present in an amount of from 0.2 to 3 wt % based on the total weight of the crystalline powder. In one aspect nicotine is present in an amount of from 0.5 to 3 wt % based on the total weight of the crystalline powder. In one aspect nicotine is present in an amount of from 1 to 3 wt % based on the total weight of the crystalline powder.

In one aspect nicotine is present in an amount of no greater than 2 wt % based on the total weight of the crystalline powder. In one aspect nicotine is present in an amount of from 0.01 to 2 wt % based on the total weight of the crystalline powder. In one aspect nicotine is present in an amount of from 0.02 to 2 wt % based on the total weight of the crystalline powder. In one aspect nicotine is present in an amount of from 0.05 to 2 wt % based on the total weight of the crystalline powder. In one aspect nicotine is present in an amount of from 0.08 to 2 wt % based on the total weight of the crystalline powder. In one aspect nicotine is present in an amount of from 0.1 to 2 wt % based on the total weight of the crystalline powder. In one aspect nicotine is present in an amount of from 0.2 to 2 wt % based on the total weight of the crystalline powder. In one aspect nicotine is present in an amount of from 0.5 to 2 wt % based on the total weight of the crystalline powder. In one aspect nicotine is present in an amount of from 1 to 2 wt % based on the total weight of the crystalline powder.

In one aspect nicotine is present in an amount of no greater than 90 wt % based on the total weight of the gel. In one aspect nicotine is present in an amount of from 1 to 90 wt % based on the total weight of the gel. In one aspect nicotine is present in an amount of from 5 to 90 wt % based on the total weight of the gel. In one aspect nicotine is present in an amount of from 10 to 90 wt % based on the total weight of the gel. In one aspect nicotine is present in an amount of from 15 to 90 wt % based on the total weight of the gel. In one aspect nicotine is present in an amount of from 20 to 90 wt % based on the total weight of the gel. In one aspect nicotine is present in an amount of from 25 to 90 wt % based on the total weight of the gel. In one aspect nicotine is present in an amount of from 30 to 90 wt % based on the total weight of the gel. In one aspect nicotine is present in an amount of from 35 to 90 wt % based on the total weight of the gel. In one aspect nicotine is present in an amount of from 40 to 90 wt % based on the total weight of the gel. In one aspect nicotine is present in an amount of from 45 to 90 wt % based on the total weight of the gel. In one aspect nicotine is present in an amount of from 50 to 90 wt % based on the total weight of the gel. In one aspect nicotine is present in an amount of from 60 to 90 wt % based on the total weight of the gel. In one aspect nicotine is present in an amount of from 70 to 90 wt % based on the total weight of the gel. In one aspect nicotine is present in an amount of from 80 to 90 wt % based on the total weight of the gel.

In one aspect nicotine is present in an amount of no greater than 85 wt % based on the total weight of the gel. In one aspect nicotine is present in an amount of from 1 to 85 wt % based on the total weight of the gel. In one aspect nicotine is present in an amount of from 5 to 85 wt % based on the total weight of the gel. In one aspect nicotine is present in an amount of from 10 to 85 wt % based on the total weight of the gel. In one aspect nicotine is present in an amount of from 15 to 85 wt % based on the total weight of the gel. In one aspect nicotine is present in an amount of from 20 to 85 wt % based on the total weight of the gel. In one aspect nicotine is present in an amount of from 25 to 85 wt % based on the total weight of the gel. In one aspect nicotine is present in an amount of from 30 to 85 wt % based on the total weight of the gel. In one aspect nicotine is present in an amount of from 35 to 85 wt % based on the total weight of the gel. In one aspect nicotine is present in an amount of from 40 to 85 wt % based on the total weight of the gel. In one aspect nicotine is present in an amount of from 45 to 85 wt % based on the total weight of the gel. In one aspect nicotine is present in an amount of from 50 to 85 wt % based on the total weight of the gel.

In one aspect nicotine is present in an amount of no greater than 80 wt % based on the total weight of the gel. In one aspect nicotine is present in an amount of from 1 to 80 wt % based on the total weight of the gel. In one aspect nicotine is present in an amount of from 5 to 80 wt % based on the total weight of the gel. In one aspect nicotine is present in an amount of from 10 to 80 wt % based on the total weight of the gel. In one aspect nicotine is present in an amount of from 15 to 80 wt % based on the total weight of the gel. In one aspect nicotine is present in an amount of from 20 to 80 wt % based on the total weight of the gel. In one aspect nicotine is present in an amount of from 25 to 80 wt % based on the total weight of the gel. In one aspect nicotine is present in an amount of from 30 to 80 wt % based on the total weight of the gel. In one aspect nicotine is present in an amount of from 35 to 80 wt % based on the total weight of the gel. In one aspect nicotine is present in an amount of from 40 to 80 wt % based on the total weight of the gel. In one aspect nicotine is present in an amount of from 45 to 80 wt % based on the total weight of the gel. In one aspect nicotine is present in an amount of from 50 to 80 wt % based on the total weight of the gel. In one aspect nicotine is present in an amount of from 60 to 80 wt % based on the total weight of the gel. In one aspect nicotine is present in an amount of from 70 to 80 wt % based on the total weight of the gel.

In one aspect nicotine is present in an amount of no greater than 75 wt % based on the total weight of the gel. In one aspect nicotine is present in an amount of from 1 to 75 wt % based on the total weight of the gel. In one aspect nicotine is present in an amount of from 5 to 75 wt % based on the total weight of the gel. In one aspect nicotine is present in an amount of from 10 to 75 wt % based on the total weight of the gel. In one aspect nicotine is present in an amount of from 15 to 75 wt % based on the total weight of the gel. In one aspect nicotine is present in an amount of from 20 to 75 wt % based on the total weight of the gel. In one aspect nicotine is present in an amount of from 25 to 75 wt % based on the total weight of the gel. In one aspect nicotine is present in an amount of from 30 to 75 wt % based on the total weight of the gel. In one aspect nicotine is present in an amount of from 35 to 75 wt % based on the total weight of the gel. In one aspect nicotine is present in an amount of from 40 to 75 wt % based on the total weight of the gel. In one aspect nicotine is present in an amount of from 45 to 75 wt % based on the total weight of the gel. In one aspect nicotine is present in an amount of from 50 to 75 wt % based on the total weight of the gel.

In one aspect nicotine is present in an amount of no greater than 70 wt % based on the total weight of the gel. In one aspect nicotine is present in an amount of from 1 to 70 wt % based on the total weight of the gel. In one aspect nicotine is present in an amount of from 5 to 70 wt % based on the total weight of the gel. In one aspect nicotine is present in an amount of from 10 to 70 wt % based on the total weight of the gel. In one aspect nicotine is present in an amount of from 15 to 70 wt % based on the total weight of the gel. In one aspect nicotine is present in an amount of from 20 to 70 wt % based on the total weight of the gel. In one aspect nicotine is present in an amount of from 25 to 70 wt % based on the total weight of the gel. In one aspect nicotine is present in an amount of from 30 to 70 wt % based on the total weight of the gel. In one aspect nicotine is present in an amount of from 35 to 70 wt % based on the total weight of the gel. In one aspect nicotine is present in an amount of from 40 to 70 wt % based on the total weight of the gel. In one aspect nicotine is present in an amount of from 45 to 70 wt % based on the total weight of the gel. In one aspect nicotine is present in an amount of from 50 to 70 wt % based on the total weight of the gel. In one aspect nicotine is present in an amount of from 60 to 70 wt % based on the total weight of the gel.

In one aspect nicotine is present in an amount of no greater than 60 wt % based on the total weight of the gel. In one aspect nicotine is present in an amount of from 1 to 60 wt % based on the total weight of the gel. In one aspect nicotine is present in an amount of from 5 to 60 wt % based on the total weight of the gel. In one aspect nicotine is present in an amount of from 10 to 60 wt % based on the total weight of the gel. In one aspect nicotine is present in an amount of from 15 to 60 wt % based on the total weight of the gel. In one aspect nicotine is present in an amount of from 20 to 60 wt % based on the total weight of the gel. In one aspect nicotine is present in an amount of from 25 to 60 wt % based on the total weight of the gel. In one aspect nicotine is present in an amount of from 30 to 60 wt % based on the total weight of the gel. In one aspect nicotine is present in an amount of from 35 to 60 wt % based on the total weight of the gel. In one aspect nicotine is present in an amount of from 40 to 60 wt % based on the total weight of the gel. In one aspect nicotine is present in an amount of from 45 to 60 wt % based on the total weight of the gel. In one aspect nicotine is present in an amount of from 50 to 60 wt % based on the total weight of the gel.

In one aspect nicotine is present in an amount of no greater than 50 wt % based on the total weight of the gel. In one aspect nicotine is present in an amount of from 1 to 50 wt % based on the total weight of the gel. In one aspect nicotine is present in an amount of from 5 to 50 wt % based on the total weight of the gel. In one aspect nicotine is present in an amount of from 10 to 50 wt % based on the total weight of the gel. In one aspect nicotine is present in an amount of from 15 to 50 wt % based on the total weight of the gel. In one aspect nicotine is present in an amount of from 20 to 50 wt % based on the total weight of the gel. In one aspect nicotine is present in an amount of from 25 to 50 wt % based on the total weight of the gel. In one aspect nicotine is present in an amount of from 30 to 50 wt % based on the total weight of the gel. In one aspect nicotine is present in an amount of from 35 to 50 wt % based on the total weight of the gel. In one aspect nicotine is present in an amount of from 40 to 50 wt % based on the total weight of the gel. In one aspect nicotine is present in an amount of from 45 to 50 wt % based on the total weight of the gel.

The gel or crystalline powder comprises nicotine in protonated form. The gel or crystalline powder may comprise nicotine in unprotonated form. In one aspect the gel or crystalline powder comprises nicotine in unprotonated form and nicotine in monoprotonated form. In one aspect the gel or crystalline powder comprises nicotine in unprotonated form and nicotine in diprotonated form. In one aspect the gel or crystalline powder comprises nicotine in unprotonated form, nicotine in monoprotonated form and nicotine in diprotonated form.

In one aspect at least 5 wt % of the nicotine present in the gel or crystalline powder is in protonated form. In one aspect at least 10 wt % of the nicotine present in the gel or crystalline powder is in protonated form. In one aspect at least 15 wt % of the nicotine present in the gel or crystalline powder is in protonated form. In one aspect at least 20 wt % of the nicotine present in the gel or crystalline powder is in protonated form. In one aspect at least 25 wt % of the nicotine present in the gel or crystalline powder is in protonated form. In one aspect at least 30 wt % of the nicotine present in the gel or crystalline powder is in protonated form. In one aspect at least 35 wt % of the nicotine present in the gel or crystalline powder is in protonated form. In one aspect at least 40 wt % of the nicotine present in the gel or crystalline powder is in protonated form. In one aspect at least 45 wt % of the nicotine present in the gel or crystalline powder is in protonated form. In one aspect at least 50 wt % of the nicotine present in the gel or crystalline powder is in protonated form. In one aspect at least 55 wt % of the nicotine present in the gel or crystalline powder is in protonated form. In one aspect at least 60 wt % of the nicotine present in the gel or crystalline powder is in protonated form. In one aspect at least 65 wt % of the nicotine present in the gel or crystalline powder is in protonated form. In one aspect at least 70 wt % of the nicotine present in the gel or crystalline powder is in protonated form. In one aspect at least 75 wt % of the nicotine present in the gel or crystalline powder is in protonated form. In one aspect at least 80 wt % of the nicotine present in the gel or crystalline powder is in protonated form. In one aspect at least 85 wt % of the nicotine present in the gel or crystalline powder is in protonated form. In one aspect at least 90 wt % of the nicotine present in the gel or crystalline powder is in protonated form. In one aspect at least 95 wt % of the nicotine present in the gel or crystalline powder is in protonated form. In one aspect at least 99 wt % of the nicotine present in the gel or crystalline powder is in protonated form. In one aspect at least 99.9 wt % of the nicotine present in the gel or crystalline powder is in protonated form.

In one aspect from 50 to 95 wt % of the nicotine present in the gel or crystalline powder is in protonated form. In one aspect from 55 to 95 wt % of the nicotine present in the gel or crystalline powder is in protonated form. In one aspect from 60 to 95 wt % of the nicotine present in the gel or crystalline powder is in protonated form. In one aspect from 65 to 95 wt % of the nicotine present in the gel or crystalline powder is in protonated form. In one aspect from 70 to 95 wt % of the nicotine present in the gel or crystalline powder is in protonated form. In one aspect from 75 to 95 wt % of the nicotine present in the gel or crystalline powder is in protonated form. In one aspect from 80 to 95 wt % of the nicotine present in the gel or crystalline powder is in protonated form. In one aspect from 85 to 95 wt % of the nicotine present in the gel or crystalline powder is in protonated form. In one aspect from 90 to 95 wt % of the nicotine present in the gel or crystalline powder is in protonated form.

The relevant amounts of nicotine which are present in the formulation in protonated form are specified herein. These amounts may be readily calculated by one skilled in the art. Nicotine, 3-(1-methylpyrrolidin-2-yl) pyridine, is a diprotic base with pKa of 3.12 for the pyridine ring and 8.02 for the pyrrolidine ring It can exist in pH-dependent protonated (mono- and di-) and non-protonated (free base) forms which have different bioavailability.

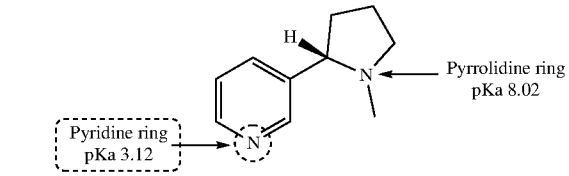

The distribution of protonated and non-protonated nicotine will vary at various pH increments.

The fraction of non-protonated nicotine will be predominant at high pH levels whilst a decrease in the pH will see an increase of the fraction of protonated nicotine (mono- or di-depending on the pH). If the relative fraction of protonated nicotine and the total amount of nicotine in the sample are known, the absolute amount of protonated nicotine can be calculated.

The relative fraction of protonated nicotine in formulation can be calculated by using the Henderson-Hasselbalch equation, which describes the pH as a derivation of the acid dissociation constant equation, and it is extensively employed in chemical and biological systems. Consider the following equilibrium:

$$B + H^+ \rightleftharpoons BH^+$$

The Henderson-Hasselbalch equation for this equilibrium is:

$$\mathrm{pH} = pKa + \log\frac{[B]}{[BH\,+]}$$

Where [B] is the amount of non-protonated nicotine (i.e. free base), [BH+] the amount of protonated nicotine (i.e. conjugate acid) and pKa is the reference pKa value for the pyrrolidine ring nitrogen of nicotine (pKa=8.02). The relative fraction of protonated nicotine can be derived from the alpha value of the non-protonated nicotine calculated from the Henderson-Hasselbalch equation as:

$$\% \text{ protonated nicotine} = 100 - \left\{ \frac{\frac{[B]}{[BH+]}}{\left\{1 + \frac{[B]}{[BH+]}\right\}} * 100 \right\}$$

Determination of pKa values of nicotine formulations was carried out using the basic approach described in "Spectroscopic investigations into the acid-base properties of nicotine at different temperatures", Peter M. Clayton, Carl A. Vas, Tam T. T. Bui, Alex F. Drake and Kevin McAdam, Anal. Methods, 2013, 5, 81-88.

Acid

As discussed herein, each of the gel and the crystalline powder contain an acid which is water soluble. By the term "water soluble" it is meant the acid has a solubility in water of at least 20 g/L at 20° C. In one aspect the acid has a solubility in water of at least 50 g/L at 20° C. In one aspect the acid has a solubility in water of at least 100 g/L at 20° C. In one aspect the acid has a solubility in water of at least 200 g/L at 20° C. In one aspect the acid has a solubility in water of at least 300 g/L at 20° C. In one aspect the acid has a solubility in water of at least 400 g/L at 20° C. In one aspect the acid has a solubility in water of at least 500 g/L at 20° C. In one aspect the acid has a solubility in water of at least 600 g/L at 20° C. In one aspect the acid has a solubility in water of at least 700 g/L at 20° C. In one aspect the acid has a solubility in water of at least 800 g/L at 20° C. In one aspect the acid has a solubility in water of at least 900 g/L at 20° C. In one aspect the acid has a solubility in water of at least 1000 g/L at 20° C. In one aspect the acid has a solubility in water of at least 1100 g/L at 20° C.

In one aspect the acid is an organic acid. In one aspect the acid is a carboxylic acid. In one aspect the acid is an organic carboxylic acid.

In one aspect the acid is selected from the group consisting of acetic acid, lactic acid, formic acid, citric acid, benzoic acid, pyruvic acid, levulinic acid, succinic acid, tartaric acid, sorbic acid, propionic acid, phenylacetic acid, and mixtures thereof. In one aspect the acid is selected from the group consisting of citric acid, benzoic acid, levulinic acid, lactic acid, sorbic acid, and mixtures thereof. In one aspect the acid is selected from the group consisting of citric acid, benzoic acid, levulinic acid, and mixtures thereof. In one aspect the acid is at least citric acid.

In one aspect the acid consists of citric acid.

In one aspect the acid is a mixture of (i) citric acid and (ii) a further acid which is not citric acid. In one aspect the acid is a mixture of (i) citric acid and (ii) a further acid selected from the group consisting of acetic acid, lactic acid, formic acid, benzoic acid, pyruvic acid, levulinic acid, succinic acid, tartaric acid, sorbic acid, propionic acid, phenylacetic acid, and mixtures thereof. In one aspect the acid is a mixture of (i) citric acid and (ii) a further acid selected from the group consisting of benzoic acid, levulinic acid, lactic acid, sorbic acid, and mixtures thereof. In one aspect the acid is a mixture of (i) citric acid and (ii) a further acid selected from the group consisting of benzoic acid, levulinic acid, and mixtures thereof.

In one aspect the acid is selected from acids having a pKa of from 2 to 5. In one aspect the acid is a weak acid. In one aspect the acid is a weak organic acid.

The molar ratio of acid to nicotine may be selected as desired. In one aspect the molar ratio of acid to nicotine is from 5:1 to 1:5. In one aspect the molar ratio of acid to nicotine is from 4:1 to 1:4. In one aspect the molar ratio of acid to nicotine is from 3:1 to 1:3. In one aspect the molar ratio of acid to nicotine is from 2:1 to 1:2. In one aspect the molar ratio of acid to nicotine is from 1.5:1 to 1:1.5. In one aspect the molar ratio of acid to nicotine is from 1.2:1 to 1:1.2. In one aspect the molar ratio of acid to nicotine is from 5:1 to 1:1. In one aspect the molar ratio of acid to nicotine is from 4:1 to 1:1. In one aspect the molar ratio of acid to nicotine is from 3:1 to 1:1. In one aspect the molar ratio of acid to nicotine is from 2:1 to 1:1. In one aspect the molar ratio of acid to nicotine is from 1.5:1 to 1:1. In one aspect the molar ratio of acid to nicotine is from 1.2:1 to 1:1.

In one aspect the total content of acid present in the gel or crystalline powder is no greater than 5 mole equivalents based on the nicotine. In one aspect the total content of acid present in the gel or crystalline powder is no greater than 4 mole equivalents based on the nicotine. In one aspect the total content of acid present in the gel or crystalline powder is no greater than 3 mole equivalents based on the nicotine. In one aspect the total content of acid present in the gel or crystalline powder is no greater than 2 mole equivalents based on the nicotine. In one aspect the total content of acid present in the gel or crystalline powder is no greater than 1 mole equivalents based on the nicotine.

In one aspect the total content of acid present in the gel or crystalline powder is no less than 0.1 mole equivalents based on the nicotine. In one aspect the total content of acid present in the gel or crystalline powder is no less than 0.2 mole equivalents based on the nicotine. In one aspect the total content of acid present in the gel or crystalline powder is no less than 0.3 mole equivalents based on the nicotine. In one aspect the total content of acid present in the gel or crystalline powder is no less than 0.4 mole equivalents based on the nicotine. In one aspect the total content of acid present in the gel or crystalline powder is no less than 0.5 mole equivalents based on the nicotine. In one aspect the total content of acid present in the gel or crystalline powder is no less than 0.7 mole equivalents based on the nicotine.

In one aspect the acid is present in an amount of no greater than 6 wt % based on the total weight of the gel or crystalline powder. In one aspect the acid is present in an amount of from 0.01 to 6 wt % based on the total weight of the gel or crystalline powder. In one aspect the acid is present in an amount of from 0.02 to 6 wt % based on the total weight of the gel or crystalline powder. In one aspect the acid is present in an amount of from 0.05 to 6 wt % based on the total weight of the gel or crystalline powder. In one aspect the acid is present in an amount of from 0.08 to 6 wt % based on the total weight of the gel or crystalline powder. In one aspect the acid is present in an amount of from 0.01 to 5 wt % based on the total weight of the gel or crystalline powder. In one aspect the acid is present in an amount of from 0.02 to 5 wt % based on the total weight of the gel or crystalline powder. In one aspect the acid is present in an amount of from 0.05 to 5 wt % based on the total weight of the gel or crystalline powder. In one aspect the acid is present in an amount of from 0.08 to 5 wt % based on the total weight of the gel or crystalline powder. In one aspect the acid is present in an amount of no greater than 4 wt % based on the total weight of the gel or crystalline powder. In one aspect the acid is present in an amount of from 0.01 to 4 wt % based on the total weight of the gel or crystalline powder. In one aspect the acid is present in an amount of from 0.02 to 4 wt % based on the total weight of the gel or crystalline powder. In one aspect the acid is present in an amount of from 0.05 to 4 wt % based on the total weight of the gel or crystalline powder. In one aspect the acid is present in an amount of from 0.08 to 4 wt % based on the total weight of the gel or crystalline powder. In one aspect the acid is present in an amount of no greater than 3 wt % based on the total weight of the gel or crystalline powder. In one aspect the acid is present in an amount of from 0.01 to 3 wt % based on the total weight of the gel or crystalline powder. In one aspect the acid is present in an amount of from 0.02 to 3 wt % based on the total weight of the gel or crystalline powder. In one aspect the acid is present in an amount of from 0.05 to 3 wt % based on the total weight of the gel or crystalline powder. In one aspect the acid is present in an amount of from 0.08 to 3 wt % based on the total weight of the gel or crystalline powder. In one aspect the acid is present in an amount of no greater than 2 wt % based on the total weight of the gel or crystalline powder. In one aspect the acid is present in an amount of from 0.01 to 2 wt % based on the total weight of the gel or crystalline powder. In one aspect the acid is present in an amount of from 0.02 to 2 wt % based on the total weight of the gel or crystalline powder. In one aspect the acid is present in an amount of from 0.05 to 2 wt % based on the total weight of the gel or crystalline powder. In one aspect the acid is present in an amount of from 0.08 to 2 wt % based on the total weight of the gel or crystalline powder. In one aspect the acid is present in an amount of no greater than 1 wt % based on the total weight of the gel or crystalline powder. In one aspect the acid is present in an amount of from 0.01 to 1 wt % based on the total weight of the gel or crystalline powder. In one aspect the acid is present in an amount of from 0.02 to 1 wt % based on the total weight of the gel or crystalline powder. In one aspect the acid is present in an amount of from 0.05 to 1 wt % based on the total weight of the gel or crystalline powder. In one aspect the acid is present in an amount of from 0.08 to 1 wt % based on the total weight of the gel or crystalline powder. In one aspect the acid is present in an amount of from 0.1 to 1 wt % based on the total weight of the gel or crystalline powder. In one aspect the acid is present in an amount of no greater than 0.6 wt % based on the total weight of the gel or crystalline powder. In one aspect the acid is present in an amount of from 0.01 to 0.6 wt % based on the total weight of the gel or crystalline powder. In one aspect the acid is present in an amount of from 0.02 to 0.6 wt % based on the total weight of the gel or crystalline powder. In one aspect the acid is present in an amount of from 0.05 to 0.6 wt % based on the total weight of the gel or crystalline powder. In one aspect the acid is present in an amount of from 0.08 to 0.6 wt % based on the total weight of the gel or crystalline powder. In one aspect the acid is present in an amount of from 0.1 to 0.6 wt % based on the total weight of the gel or crystalline powder. In one aspect the acid is present in an amount of no greater than 0.5 wt % based on the total weight of the gel or crystalline powder. In one aspect the acid is present in an amount of from 0.01 to 0.5 wt % based on the total weight of the gel or crystalline powder. In one aspect the acid is present in an amount of from 0.02 to 0.5 wt % based on the total weight of the gel or crystalline powder. In one aspect the acid is present in an amount of from 0.05 to 0.5 wt % based on the total weight of the gel or crystalline powder. In one aspect the acid is present in an amount of from 0.08 to 0.5 wt % based on the total weight of the gel or crystalline powder. In one aspect the acid is present in an amount of no greater than 0.2 wt % based on the total weight of the gel or crystalline powder. In one aspect the acid is present in an amount of from 0.01 to 0.2 wt % based on the total weight of the gel or crystalline powder. In one aspect the acid is present in an amount of from 0.02 to 0.2 wt % based on the total weight of the gel or crystalline powder. In one aspect the acid is present in an amount of from 0.05 to 0.2 wt % based on the total weight of the gel or crystalline powder. In one aspect the acid is present in an amount of from 0.08 to 0.2 wt % based on the total weight of the gel or crystalline powder. In one aspect the acid is present in an amount of no greater than 0.1 wt % based on the total weight of the gel or crystalline powder. In one aspect the acid is present in an amount of from 0.01 to 0.1 wt % based on the total weight of the gel or crystalline powder. In one aspect the acid is present in an amount of from 0.02 to 0.1 wt % based on the total weight of the gel or crystalline powder. In one aspect the acid is present in an amount of from 0.05 to 0.1 wt % based on the total weight of the gel or crystalline powder. In one aspect the acid is present in an amount of from 0.08 to 0.1 wt % based on the total weight of the gel or crystalline powder.

In one aspect the acid is present in an amount of no greater than 60 wt % based on the total weight of the gel or crystalline powder. In one aspect the acid is present in an amount of from 0.1 to 60 wt % based on the total weight of the gel or crystalline powder. In one aspect the acid is present in an amount of from 0.2 to 60 wt % based on the total weight of the gel or crystalline powder. In one aspect the acid is present in an amount of from 0.5 to 60 wt % based on the total weight of the gel or crystalline powder. In one aspect the acid is present in an amount of from 0.8 to 60 wt % based on the total weight of the gel or crystalline powder. In one aspect the acid is present in an amount of from 0.1 to 50 wt % based on the total weight of the gel or crystalline powder. In one aspect the acid is present in an amount of from 0.2 to 50 wt % based on the total weight of the gel or crystalline powder. In one aspect the acid is present in an amount of from 0.5 to 50 wt % based on the total weight of the gel or crystalline powder. In one aspect the acid is present in an amount of from 0.8 to 50 wt % based on the total weight of the gel or crystalline powder. In one aspect the acid is present in an amount of no greater than 40 wt % based on the total weight of the gel or crystalline powder. In one aspect the acid is present in an amount of from 0.1 to 40 wt % based on the total weight of the gel or crystalline powder. In one aspect the acid is present in an amount of from 0.2 to 40 wt % based on the total weight of the gel or crystalline powder. In one aspect the acid is present in an amount of from 0.5 to 40 wt % based on the total weight of the gel or crystalline powder. In one aspect the acid is present in an amount of from 0.8 to 40 wt % based on the total weight of the gel or crystalline powder. In one aspect the acid is present in an amount of no greater than 30 wt % based on the total weight of the gel or crystalline powder. In one aspect the acid is present in an amount of from 0.1 to 30 wt % based on the total weight of the gel or crystalline powder. In one aspect the acid is present in an amount of from 0.2 to 30 wt % based on the total weight of the gel or crystalline powder. In one aspect the acid is present in an amount of from 0.5 to 30 wt % based on the total weight of the gel or crystalline powder. In one aspect the acid is present in an amount of from 0.8 to 30 wt % based on the total weight of the gel or crystalline powder. In one aspect the acid is present in an amount of no greater than 20 wt % based on the total weight of the gel or crystalline powder. In one aspect the acid is present in an amount of from 0.1 to 20 wt % based on the total weight of the gel or crystalline powder. In one aspect the acid is present in an amount of from 0.2 to 20 wt % based on the total weight of the gel or crystalline powder. In one aspect the acid is present in an amount of from 0.5 to 20 wt % based on the total weight of the gel or crystalline powder. In one aspect the acid is present in an amount of from 0.8 to 20 wt % based on the total weight of the gel or crystalline powder. In one aspect the acid is present in an amount of no greater than 10 wt % based on the total weight of the gel or crystalline powder. In one aspect the acid is present in an amount of from 0.1 to 10 wt % based on the total weight of the gel or crystalline powder. In one aspect the acid is present in an amount of from 0.2 to 10 wt % based on the total weight of the gel or crystalline powder. In one aspect the acid is present in an amount of from 0.5 to 10 wt % based on the total weight of the gel or crystalline powder. In one aspect the acid is present in an amount of from 0.8 to 10 wt % based on the total weight of the gel or crystalline powder. In one aspect the acid is present in an amount of from 1 to 10 wt % based on the total weight of the gel or crystalline powder. In one aspect the acid is present in an amount of no greater than 6 wt % based on the total weight of the gel or crystalline powder. In one aspect the acid is present in an amount of from 0.1 to 6 wt % based on the total weight of the gel or crystalline powder. In one aspect the acid is present in an amount of from 0.2 to 6 wt % based on the total weight of the gel or crystalline powder. In one aspect the acid is present in an amount of from 0.5 to 6 wt % based on the total weight of the gel or crystalline powder. In one aspect the acid is present in an amount of from 0.8 to 6 wt % based on the total weight of the gel or crystalline powder. In one aspect the acid is present in an amount of from 1 to 6 wt % based on the total weight of the gel or crystalline powder. In one aspect the acid is present in an amount of no greater than 5 wt % based on the total weight of the gel or crystalline powder. In one aspect the acid is present in an amount of from 0.1 to 5 wt % based on the total weight of the gel or crystalline powder. In one aspect the acid is present in an amount of from 0.2 to 5 wt % based on the total weight of the gel or crystalline powder. In one aspect the acid is present in an amount of from 0.5 to 5 wt % based on the total weight of the gel or crystalline powder. In one aspect the acid is present in an amount of from 0.8 to 5 wt % based on the total weight of the gel or crystalline powder. In one aspect the acid is present in an amount of no greater than 2 wt % based on the total weight of the gel or crystalline powder. In one aspect the acid is present in an amount of from 0.1 to 2 wt % based on the total weight of the gel or crystalline powder. In one aspect the acid is present in an amount of from 0.2 to 2 wt % based on the total weight of the gel or crystalline powder. In one aspect the acid is present in an amount of from 0.5 to 2 wt % based on the total weight of the gel or crystalline powder. In one aspect the acid is present in an amount of from 0.8 to 2 wt % based on the total weight of the gel or crystalline powder. In one aspect the acid is present in an amount of no greater than 1 wt % based on the total weight of the gel or crystalline powder. In one aspect the acid is present in an amount of from 0.1 to 1 wt % based on the total weight of the gel or crystalline powder. In one aspect the acid is present in an amount of from 0.2 to 1 wt % based on the total weight of the gel or crystalline powder. In one aspect the acid is present in an amount of from 0.5 to 1 wt % based on the total weight of the gel or crystalline powder. In one aspect the acid is present in an amount of from 0.8 to 1 wt % based on the total weight of the gel or crystalline powder.

The amount of acid and the solubility of the acid may be selected such that a given amount of the acid will dissolve in the water. In one aspect at 20° C. at least 20% of the acid dissolves in the water. In one aspect at 25° C. at least 20% of the acid dissolves in the water. In one aspect at 30° C. at least 20% of the acid dissolves in the water. In one aspect at 20° C. at least 35% of the acid dissolves in the water. In one aspect at 20° C. at least 40% of the acid dissolves in the water. In one aspect at 20° C. at least 45% of the acid dissolves in the water. In one aspect at 20° C. at least 50% of the acid dissolves in the water. In one aspect at 20° C. at least 55% of the acid dissolves in the water.

In one aspect the acid is selected from acids which are solid at 25° C.

Flavor

As discussed herein, the crystalline powder comprises one or more flavors or flavoring components. In one aspect the gel further comprises one or more flavors or flavoring components. As used herein, the terms "flavor" and "flavorant" refer to materials which, where local regulations permit, may be used to create a desired taste or aroma in a product for adult consumers. They may include extracts (e.g. liquorice, hydrangea, Japanese white bark magnolia leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, *cassia*, caraway, cognac, jasmine, ylang-ylang, sage, fennel, piment, ginger, anise, coriander, coffee, or a mint oil from any species of the genus Mentha), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, or powder. The one or more flavors may be selected from the group consisting of (4-(para-)methoxyphenyl)-2-butanone, vanillin, γ-undecalactone, menthone, 5-propenyl guaethol, menthol, para-mentha-8-thiol-3-one and mixtures thereof. In one aspect the flavor is at least menthol.

If present, the one or more flavors may be present in any suitable amount. In one aspect the one or more flavors are present in a total amount of no greater than 10 wt. % based on the gel or crystalline powder. In one aspect the one or more flavors are present in a total amount of no greater than 7 wt. % based on the gel or crystalline powder. In one aspect the one or more flavors are present in a total amount of no greater than 5 wt. % based on the gel or crystalline powder. In one aspect the one or more flavors are present in a total amount of no greater than 4 wt. % based on the gel or crystalline powder. In one aspect the one or more flavors are present in a total amount of no greater than 3 wt. % based on the gel or crystalline powder. In one aspect the one or more flavors are present in a total amount of no greater than 2 wt. % based on the gel or crystalline powder. In one aspect the one or more flavors are present in a total amount of no greater than 1 wt. % based on the gel or crystalline powder.

In one aspect the one or more flavors are present in a total amount of from 0.01 to 5 wt. % based on the gel or crystalline powder. In one aspect the one or more flavors are present in a total amount of from 0.01 to 4 wt. % based on the gel or crystalline powder. In one aspect the one or more flavors are present in a total amount of from 0.01 to 3 wt. % based on the gel or crystalline powder. In one aspect the one or more flavors are present in a total amount of from 0.01 to 2 wt. % based on the gel or crystalline powder. In one aspect the one or more flavors are present in a total amount of from 0.01 to 1 wt. % based on the gel or crystalline powder. In one aspect the one or more flavors are present in a total amount of from 0.01 to 0.5 wt. % based on the gel or crystalline powder.

Encapsulating Material

As discussed herein, the crystalline powder comprises an encapsulating material. The encapsulating material may be present in any suitable amount in the crystalline powder.

In one aspect the encapsulating material is present in a total amount of no greater than 12 wt. % based on the crystalline powder. In one aspect the encapsulating material is present in a total amount of no greater than 10 wt. % based on the crystalline powder. In one aspect the encapsulating material is present in a total amount of no greater than 9 wt. % based on the crystalline powder. In one aspect the encapsulating material is present in a total amount of no greater than 8 wt. % based on the crystalline powder. In one aspect the encapsulating material is present in a total amount of no greater than 7 wt. % based on the crystalline powder. In one aspect the encapsulating material is present in a total amount of no greater than 6 wt. % based on the crystalline powder. In one aspect the encapsulating material is present in a total amount of no greater than 5 wt. % based on the crystalline powder. In one aspect the encapsulating material is present in a total amount of no greater than 4 wt. % based on the crystalline powder. In one aspect the encapsulating material is present in a total amount of no greater than 3 wt. % based on the crystalline powder.

In one aspect the one or more encapsulating materials is selected from the group consisting of micelles, cyclodextrins, calixarenes, metal organic frameworks, dendrimers, polymers, hydrocolloids, pollen spores, yeast particles, porous silica, and mixtures thereof. In one aspect the one or more encapsulating materials are selected from cyclodextrins and mixtures thereof.

The one or more cyclodextrins may be selected from the group consisting of unsubstituted cyclodextrins, substituted cyclodextrins and mixtures thereof. In one aspect at least one cyclodextrin is an unsubstituted cyclodextrin. In one aspect the one or more cyclodextrins are selected from the group consisting of unsubstituted cyclodextrins. In one aspect at least one cyclodextrin is a substituted cyclodextrin. In one aspect the one or more cyclodextrins are selected from the group consisting of substituted cyclodextrins.

In one aspect the one or more cyclodextrins are selected from the group consisting of unsubstituted ($\alpha$)-cyclodextrin, substituted ($\alpha$)-cyclodextrin, unsubstituted ($\beta$)-cyclodextrin, substituted ($\beta$)-cyclodextrin, unsubstituted ($\gamma$)-cyclodextrin, substituted ($\gamma$)-cyclodextrin, and mixtures thereof. In one aspect the one or more cyclodextrins are selected from the group consisting of unsubstituted ($\beta$)-cyclodextrin, substituted ($\beta$)-cyclodextrin, and mixtures thereof.

In one aspect the one or more cyclodextrins are selected from the group consisting of unsubstituted ($\alpha$)-cyclodextrin, unsubstituted ($\beta$)-cyclodextrin, unsubstituted ($\gamma$)-cyclodextrin, and mixtures thereof. In one aspect the one or more cyclodextrins is selected from unsubstituted ($\beta$)-cyclodextrin.

In one aspect the one or more cyclodextrins are selected from the group consisting of substituted ($\alpha$)-cyclodextrin, substituted ($\beta$)-cyclodextrin, substituted ($\gamma$)-cyclodextrin, and mixtures thereof. In one aspect the one or more cyclodextrins is selected from substituted ($\beta$)-cyclodextrins. Chemical substitutions at the 2-, 3-, and 6-hydroxyl sites are envisaged, and in particular substitution at the 2-position.

In one aspect the one or more cyclodextrins are selected from the group consisting of 2-hydroxy-propyl-$\alpha$-cyclodextrin, 2-hydroxy-propyl-$\beta$-cyclodextrin, 2-hydroxy-propyl-$\gamma$-cyclodextrin and mixtures thereof. In one aspect the one or more cyclodextrins is at least 2-hydroxy-propyl-$\alpha$-cyclodextrin. In one aspect the one or more cyclodextrins is at least 2-hydroxy-propyl-$\beta$-cyclodextrin. In one aspect the one or more cyclodextrins is at least 2-hydroxy-propyl-$\gamma$-cyclodextrin.

2-hydroxy-propyl derivatives of cyclodextrins, such as 2-hydroxy-propyl-O-cyclodextrin have increased solubility in water when compared to base cyclodextrins such as $\beta$-cyclodextrin.

The one or more cyclodextrins may or may not be present in any suitable amount in the crystalline powder. In one aspect the one or more cyclodextrins are present in a total amount of no greater than 12 wt. % based on the crystalline powder. In one aspect the one or more cyclodextrins are present in a total amount of no greater than 10 wt. % based on the crystalline powder. In one aspect the one or more cyclodextrins are present in a total amount of no greater than 9 wt. % based on the crystalline powder. In one aspect the one or more cyclodextrins are present in a total amount of no greater than 8 wt. % based on the crystalline powder. In one aspect the one or more cyclodextrins are present in a total amount of no greater than 7 wt. % based on the crystalline powder. In one aspect the one or more cyclodextrins are present in a total amount of no greater than 6 wt. % based on the crystalline powder. In one aspect the one or more cyclodextrins are present in a total amount of no greater than 5 wt. % based on the crystalline powder. In one aspect the one or more cyclodextrins are present in a total amount of no greater than 4 wt. % based on the crystalline powder. In one aspect the one or more cyclodextrins are present in a total amount of no greater than 3 wt. % based on the crystalline powder.

Process

As discussed herein, in one aspect there is provided a process for forming a gel comprising
(i) water in an amount of from 1 to 20 wt. % based on the gel;
(ii) nicotine; and
(iii) a water soluble acid;
the process comprising the steps of:
(a) providing a nicotine solution comprising
(i) water in an amount of from 50 to 90 wt. % based on the nicotine solution;
(ii) nicotine; and
(iii) the water soluble acid;
(b) dehydrating the nicotine solution to provide the gel.

As discussed herein, in one aspect there is provided a process for forming a crystalline powder comprising
(i) water in an amount of less than 15 wt % based on the crystalline powder;
(ii) nicotine;
(iii) a water soluble acid;
(iv) one or more flavors; and
(v) an encapsulating material.
the process comprising the steps of:
(a) providing a nicotine solution comprising
(i) water in an amount of from 50 to 95 wt. % based on the nicotine solution;
(ii) nicotine;
(iii) a water soluble acid;

(iv) one or more flavors; and
(v) an encapsulating material;
(b) dehydrating the nicotine solution to provide the crystalline powder.

In one aspect, in the process for forming a gel there is provided a nicotine solution comprising water in an amount of from 55 to 90 wt. % based on the nicotine solution. In one aspect, in the process for forming a gel there is provided a nicotine solution comprising water in an amount of from 60 to 90 wt. % based on the nicotine solution. In one aspect, in the process for forming a gel there is provided a nicotine solution comprising water in an amount of from 65 to 90 wt. % based on the nicotine solution. In one aspect, in the process for forming a gel there is provided a nicotine solution comprising water in an amount of from 70 to 90 wt. % based on the nicotine solution. In one aspect, in the process for forming a gel there is provided a nicotine solution comprising water in an amount of from 75 to 90 wt. % based on the nicotine solution. In one aspect, in the process for forming a gel there is provided a nicotine solution comprising water in an amount of from 75 to 85 wt. % based on the nicotine solution.

In one aspect, in the process for forming a crystalline powder there is provided a nicotine solution comprising water in an amount of from 55 to 95 wt. % based on the nicotine solution. In one aspect, in the process for forming a crystalline powder there is provided a nicotine solution comprising water in an amount of from 60 to 95 wt. % based on the nicotine solution. In one aspect, in the process for forming a crystalline powder there is provided a nicotine solution comprising water in an amount of from 65 to 95 wt. % based on the nicotine solution. In one aspect, in the process for forming a crystalline powder there is provided a nicotine solution comprising water in an amount of from 70 to 95 wt. % based on the nicotine solution. In one aspect, in the process for forming a crystalline powder there is provided a nicotine solution comprising water in an amount of from 75 to 95 wt. % based on the nicotine solution. In one aspect, in the process for forming a crystalline powder there is provided a nicotine solution comprising water in an amount of from 80 to 95 wt. % based on the nicotine solution. In one aspect, in the process for forming a crystalline powder there is provided a nicotine solution comprising water in an amount of from 85 to 95 wt. % based on the nicotine solution. In one aspect, in the process for forming a crystalline powder there is provided a nicotine solution comprising water in an amount of from 90 to 95 wt. % based on the nicotine solution.

A typical process is described as follow.

During preparation a formulation is prepared which is stirred and warmed to approximately 40° C. This allows appropriate mixing of the components throughout the process. At this temperature, the cyclodextrin (such as (2-Hydroxypropyl)-β-cyclodextrin) is thermally stable, and should be added first. Typically a maximum loading of 10% w/w must not be exceeded. This loading will depend on the percentage flavor composition and is expected to be less to achieve 90% water inclusion.

Nicotine may then be added, with the precautionary note that since it is already miscible with water, no precipitation will be observed. Typical loading ranges are from of 0.1 and 1.2 wt %.

The flavor components should be added last; this is due to the generally higher binding energy (vs. nicotine) with the cyclodextrin host. We have found that the larger the disparity in binding energies, the less chance of a competing complexation mechanism with nicotine. For menthol example, the approximate binding energies are $-4.13$ Kcal·mol$^{-1}$ (nicotine) and $-5.06$ Kcal·mol$^{-1}$ (menthol). It is noted that, for this example, and depending on loadings, slight precipitation of menthol may be observed on cooling from 40° C. to ambient. Microfiltration may then be performed, in this case, to remove any excess menthol which has not formed a complex with cyclodextrin.

An aqueous solution of citric acid and nicotine was prepared using a 1:1 molar equivalent ratio. The resulting liquid is bright orange and shows no signs of separation. Using a desiccator, water and any water-soluble impurities are removed from the liquid, resulting in a production of a bright orange precipitate with a gel-like consistency. This may be referred to as 'nicotinium citrate' gel. The formulation can then be prepared as above, except that no heating or filtration steps are required. When the nicotinium citrate gel is added in place of nicotine in the final formulation stages, it dissociates in the corresponding nicotinium(+) and citrate(−) ions. Since nicotinium(+) is inherently larger than nicotine, (it has inherited a proton from the corresponding citrate(−) ion), it does not interfere with the menthol-cyclodextrin complexation mechanism since menthol is now the favoured guest species. Thus there is no any visual menthol precipitate. Sensorally, the formulation is more robust when prepared in this manner. Flavor delivery is optimised and no longer tails off with increasing nicotine concentration. Nicotine delivery is also optimized because the nicotine now exists in the particulate phase rather than the vapor phase, so it can penetrate the deep lung. The presence of citrate(−) ions complements the nicotine attributes by providing an inherent bitterness and enhanced throat catch. It is feasible to further reduce the nicotine concentration because of this effect.

Thus in one aspect there is provided a process for forming a crystalline powder comprising
(i) water in an amount of less than 15 wt % based on the crystalline powder;
(ii) nicotine;
(iii) a water soluble acid;
(iv) one or more flavors; and
(v) an encapsulating material;
the process comprising the steps of:
(a) providing a gel comprising
(i) water in an amount of from 1 to 20 wt. % based on the gel;
(ii) nicotine; and
(iii) a water soluble acid
(b) providing a flavor solution comprising
(iii) a water soluble acid;
(iv) one or more flavors; and
(v) an encapsulating material;
contacting the gel with the flavor solution to form a nicotine solution; and
(c) dehydrating the nicotine solution to provide the crystalline powder.

As discussed herein, in one aspect there is provided a process for rehydrating a gel comprising
(i) water in an amount of from 1 to 20 wt. % based on the gel;
(ii) nicotine; and
(iii) a water soluble acid;
the process comprising the step of contacting the gel with water.

As discussed herein, in one aspect there is provided a process for rehydrating a crystalline powder comprising
(i) water in an amount of less than 15% wt. % based on the crystalline powder;

(ii) nicotine;
(iii) a water soluble acid;
(iv) one or more flavors; and
(v) an encapsulating material;
the process comprising the step of contacting the crystalline powder with water.

The gel or crystalline powder may be contained or delivered by any means. In one aspect the present disclosure provides a contained gel or crystalline powder comprising (a) one or more containers; and (b) an gel or crystalline powder as defined herein. The container may be any suitable container, for example to allow for the storage or delivery of the gel or crystalline powder. In one aspect the container is configured for engagement with an electronic aerosol provision system. The container may be configured to become fluidly in communication with an electronic aerosol provision system so that gel or crystalline powder may be delivered to the electronic aerosol provision system. As described above, the present disclosure relates to container which may be used in an electronic aerosol provision system, such as an e-cigarette. Throughout the following description the term "e-cigarette" is used; however, this term may be used interchangeably with electronic aerosol provision system.

As discussed herein, the container of the present disclosure is typically provided for the delivery of gel or crystalline powder to or within an e-cigarette. The gel or crystalline powder may be held within an e-cigarette or may be sold as a separate container for subsequent use with or in an e-cigarette. As understood by one skilled in the art, e-cigarettes may contain a unit known as a detachable cartomizer which typically comprises a reservoir of gel or crystalline powder, a wick material and a heating element for vaporizing the gel or crystalline powder. In some e-cigarettes, the cartomizer is part of a single-piece device and is not detachable. In one aspect the container is a cartomizer or is part of a cartomizer. In one aspect the container is not a cartomizer or part of a cartomizer and is a container, such as a tank, which may be used to deliver nicotine gel or crystalline powder to or within an e-cigarette.

In one aspect the container is part of an e-cigarette. Therefore in a further aspect the present disclosure provides an electronic aerosol provision system comprising: an gel or crystalline powder as defined herein; an aerosolizer for aerosolizing gel or crystalline powder for inhalation by a user of the electronic aerosol provision system; and a power supply comprising a cell or battery for supplying power to the aerosolizer.

In addition to the gel or crystalline powder of the present disclosure and to systems such as containers and electronic aerosol provision systems containing the same, the present disclosure provides a process for improving the sensory properties of an aerosolized nicotine. In a further aspect the present disclosure provides a process for improving the storage stability of an aerosolized nicotine gel or crystalline powder.

Reference to an improvement in the sensory properties of a vaporized nicotine refer may include an improvement in the smoothness of the vaporized nicotine as perceived by a user.

The process of the present disclosure may comprises additional steps either before the steps listed, after the steps listed or between one or more of the steps listed.

The disclosure will now be described with reference to the following non-limiting examples.

EXAMPLES

Example 1

It was found by experiment that the solubility of the crystalline powder in isopropyl alcohol (IPA) was approximately 1 g/100 mL at 20° C., after vigorous agitation. 20 ml of crystalline powder extract was prepared in triplicate and analyzed for nicotine/menthol and water content via GC-FID.

N-heptadecane was added as an internal standard at a concentration of 125 mg/mL to each extract for the nicotine/menthol measurements, and Ethanol (100%) was added as an internal standard at a concentration of 125 mg/mL to each extract for the water measurements.

Menthol was measured below the reporting limit of 0.0747 mg/ml for all three samples. Two of the samples contained nicotine measured below the method reporting limit of 0.0251 mg/ml.

Water was found in all samples within constraints of the method calibration curve (0.00-0.09 mg/ml).

Example 2

Production Process of Nicotinium Citrate 5 ml aqueous solution of 0.2044 g citric acid and 0.2035 g nicotine was prepared using a 1:1 molar equivalent ratio. The resulting liquid was homogeneous and showed no signs of separation. No heating or filtration steps were required.
Dehydration Process Using a desiccator and a silica gel, water and any water-soluble impurities were removed from the liquid via vacuum over 24 hours, resulting in a production of a precipitate with a gel-like consistency. The formed gel was air dried overnight. This was referred to as 'nicotinium citrate' gel.
Combining Nicotinium Citrate with Flavor Firstly, 10 ml of aqueous solution was prepared by stirring 0.9% (w/w) menthol and 9% (w/w) 2-hydroxy-propyl-β-cyclodextrin on a hot plate at 40° C. for approximately 30 minutes. The water solution containing flavor compound and encapsulating material was then added to the dried gel and stirred for dissolution of another 30 minutes. This resulted in a homogeneous solution without any signs of separation.
Production Process of Crystalline Powder Formed solution was then dried by applying the same dehydration process over the period of 1 week which results in crystalline powder (solid) containing nicotine, flavor, encapsulating material and ~7% (w/w) water. This powder was later re-hydrated by simply adding water and stirring. After stirring for 3 minutes the powder had been fully rehydrated to provide a clear solution.

To provide sensory testing 1.5 g of the crystalline powered was dissolved in 10 ml of water by stirring for 3 minutes at room temperature. The solution provided was loaded in a commercially available nebulizer. The sensory perception of rehydrated formulation was rated by the panelists as acceptable.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the inven-

The invention claimed is:

1. A gel comprising:
   (i) water in an amount of from 1 to 20 wt. % based on the gel;
   (ii) nicotine present in an amount of from 15 to 90 wt. % based on the gel; and
   (iii) a water soluble acid having a solubility in water of at least 20 g/L at 20° C., wherein a molar ratio of the water soluble acid to the nicotine is from 3:1 to 1:3.

2. The gel according to claim 1, wherein water is present in an amount of from 1 to 15 wt. % based on the gel.

3. The gel according to claim 1, wherein water is present in an amount of from 1 to 10 wt. % based on the gel.

4. The gel according to claim 1, wherein nicotine is present in an amount of from 50 to 75 wt. % based on the gel.

5. The gel according to claim 1, wherein the molar ratio of the water soluble acid to the nicotine is from 2:1 to 1:2.

6. The gel according to claim 1, wherein the water soluble acid is selected from the group consisting of acetic acid, lactic acid, formic acid, citric acid, benzoic acid, pyruvic acid, levulinic acid, succinic acid, tartaric acid, sorbic acid, propionic acid, phenylacetic acid, and mixtures thereof.

7. The gel according to claim 1, wherein the water soluble acid is selected from the group consisting of citric acid, benzoic acid, levulinic acid, lactic acid, sorbic acid, and mixtures thereof.

8. The gel according to claim 1, wherein the water soluble acid comprises citric acid.

9. The gel of claim 1, wherein the gel is contained in a container.

10. A process for forming a gel, the process comprising the steps of:
    (a) providing a nicotine solution comprising
        (i) water in an amount of from 50 to 90 wt. % based on the nicotine solution;
        (ii) nicotine present in an amount of from 15 to 90 wt. % based on the gel; and
        (iii) a water soluble acid;
    (b) dehydrating the nicotine solution to provide the gel, wherein the gel comprises
        (i) water in an amount of from 1 to 20 wt. % based on the gel;
        (ii) nicotine present in an amount of from 15 to 90 wt. % based on the gel; and
        (iii) the water soluble acid having a solubility in water of at least 20 g/L at 20° C.;
    wherein a molar ratio of the water soluble acid to the nicotine is from 3:1 to 1:3.

11. A process for rehydrating a gel comprising the step of: contacting the gel with water, the gel comprising
    (i) water in an amount of from 1 to 20 wt. % based on the gel;
    (ii) nicotine present in an amount of from 15 to 90 wt. % based on the gel; and
    (iii) a water soluble acid having a solubility in water of at least 20 g/L at 20° C., wherein a molar ratio of acid to the nicotine is from 3:1 to 1:3.

12. The process according to claim 10, wherein water is present in an amount of from 1 to 15 wt. % based on the gel.

13. The process according to claim 10, wherein water is present in an amount of from 1 to 10 wt. % based on the gel.

14. The process according to claim 10, wherein nicotine is present in an amount of from 50 to 75 wt. % based on the gel.

15. The process according to claim 10, wherein the molar ratio of the water soluble acid to the nicotine is from 2:1 to 1:2.

16. The process according to claim 10, wherein the water soluble acid is selected from the group consisting of acetic acid, lactic acid, formic acid, citric acid, benzoic acid, pyruvic acid, levulinic acid, succinic acid, tartaric acid, sorbic acid, propionic acid, phenylacetic acid, and mixtures thereof.

17. The process according to claim 10, wherein the water soluble acid is selected from the group consisting of citric acid, benzoic acid, levulinic acid, lactic acid, sorbic acid, and mixtures thereof.

18. The process according to claim 10, wherein the water soluble acid comprises citric acid.

19. A process of using a gel to form a crystalline powder, the process comprising the steps of:
    (a) contacting a gel with a flavor solution to form a nicotine solution, wherein the gel comprises water in an amount of from 1 to 20 wt. % based on the gel, nicotine present in an amount of from 15 to 90 wt. % based on the gel, and a water soluble acid having a solubility in water of at least 20 g/L at 20° C., wherein a molar ratio of the water soluble acid to the nicotine of the gel is from 3:1 to 1:3, and wherein the flavor solution comprises a water soluble acid, one or more flavors, and an encapsulating material; and
    (b) dehydrating the nicotine solution to provide the crystalline powder, wherein the crystalline powder comprises water in an amount of less than 15 wt % based on the crystalline powder, nicotine, a water soluble acid having a solubility in water of at least 20 g/L at 20° C., one or more flavors, and an encapsulating material, wherein a molar ratio of the water soluble acid to the nicotine is from 3:1 to 1:3.

* * * * *